US012559787B2

(12) United States Patent
Krummel et al.

(10) Patent No.: US 12,559,787 B2
(45) Date of Patent: Feb. 24, 2026

(54) SINGLE CELL MAPPING AND TRANSCRIPTOME ANALYSIS

(71) Applicant: The Regents of the University of California, Oakland, CA (US)

(72) Inventors: Matthew Krummel, San Francisco, CA (US); Kenneth Hsueh-heng Hu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1247 days.

(21) Appl. No.: 17/057,569

(22) PCT Filed: May 21, 2019

(86) PCT No.: PCT/US2019/033279
§ 371 (c)(1),
(2) Date: Nov. 20, 2020

(87) PCT Pub. No.: WO2019/226631
PCT Pub. Date: Nov. 28, 2019

(65) Prior Publication Data
US 2021/0198722 A1 Jul. 1, 2021

Related U.S. Application Data

(60) Provisional application No. 62/674,607, filed on May 21, 2018.

(51) Int. Cl.
*C12Q 1/6816* (2018.01)
*B01L 3/00* (2006.01)

(52) U.S. Cl.
CPC ...... *C12Q 1/6816* (2013.01); *B01L 3/502715* (2013.01); *G01N 2570/00* (2013.01)

(58) Field of Classification Search
CPC ........... C12Q 1/6816; C12Q 2525/186; C12Q 2563/179; C12Q 1/6806; B01L 3/502715
See application file for complete search history.

(56) References Cited

U.S. PATENT DOCUMENTS

| | | | |
|---|---|---|---|
| 9,469,874 B2 | 10/2016 | Chen et al. | |
| 2007/0275047 A1 | 11/2007 | Pfeiffer | |
| 2010/0255426 A1 | 10/2010 | Jain et al. | |
| 2010/0292458 A1 | 11/2010 | Buhler et al. | |
| 2014/0066318 A1* | 3/2014 | Frisen ................. | C12Q 1/6853 |
| | | | 506/3 |
| 2014/0155295 A1* | 6/2014 | Hindson .............. | C12Q 1/6806 |
| | | | 506/4 |
| 2016/0236195 A1 | 8/2016 | Dairdon | |
| 2018/0057873 A1 | 3/2018 | Zhou et al. | |
| 2019/0292458 A1 | 9/2019 | Klass et al. | |

FOREIGN PATENT DOCUMENTS

| | | | |
|---|---|---|---|
| WO | WO2003/065038 A2 | 8/2003 | |
| WO | 2010039543 A2 | 4/2010 | |
| WO | WO-2012106385 A2 * | 8/2012 | ........... C12Q 1/6804 |
| WO | WO-2014200767 A1 * | 12/2014 | ........... C12Q 1/6804 |
| WO | 2017053905 A1 | 3/2017 | |
| WO | 2017075293 A1 | 5/2017 | |
| WO | WO-2017161325 A1 * | 9/2017 | ........... C07D 277/04 |

OTHER PUBLICATIONS

Stahl et al, 2016, Visualizationand analysis of gene expression in tissue sections by spatial transcriptomics, Science 353: 78-82.

* cited by examiner

*Primary Examiner* — Sahana S Kaup
(74) *Attorney, Agent, or Firm* — Shay Glenn LLP

(57) ABSTRACT
Methods of tagging cells with unique oligonucleotide "zip-code" constructs are provided. By these methods and associated compositions, cells in a multicellular structure such as a tissue section can be tagged with a construct, the unique composition of which is associated with the cells position in the multicellular structure. Subsequently, the multicellular structure can be dissociated into single cells and a single cell transcriptome analysis performed, as well as other types of single cell analyses. By preserving positional information in the analyzed single cells, biological processes within the tissue can be mapped. By these methods, the effects of the local environment surrounding a cell on its state and various functions can be elucidated, and intra-tissue processes can be mapped and observed. Likewise, coordinated actions by multiple cells within a tissue can be mapped and tracked over time.

15 Claims, 13 Drawing Sheets

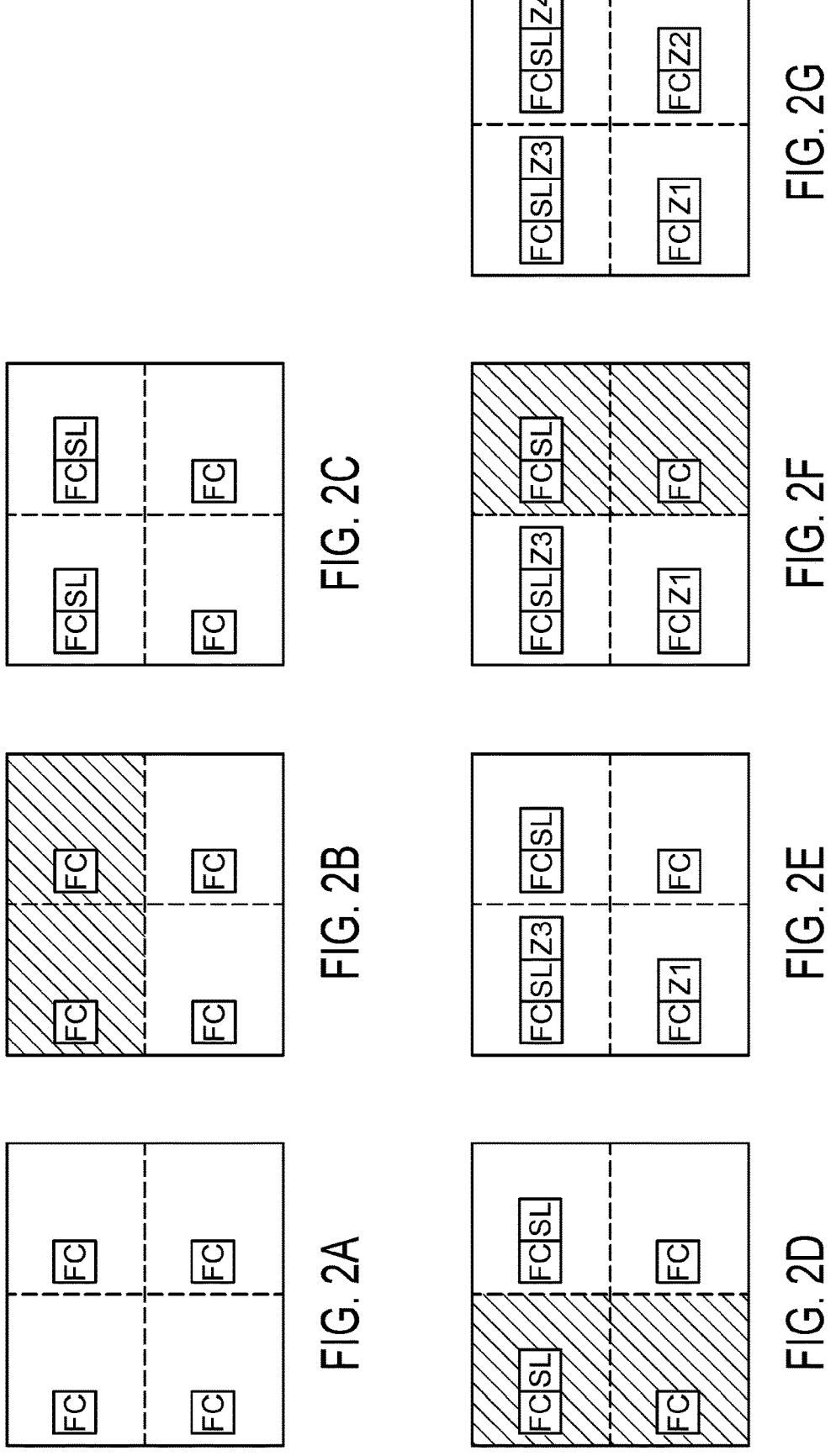

| Population | Round 1 UV illum. | Round 2 UV illum. |
|---|---|---|
| CD4T cells | + | − |
| CD8T cells | + | + |
| Macrophages | − | + |
| Dendritic cells | + | − |

|  | ZC1 UV | ZC2 UV |
|---|---|---|
| CD4T cells blasts | + | + |
| BMDC | + | + |
| CD8T cells blasts | + | − |
| BMDM | + | − |
| LB27.4's (B cell line) | − | + |
| BMDM+LPS | − | − |

FIG. 9

SINGLE CELL MAPPING AND TRANSCRIPTOME ANALYSIS

CROSS-REFERENCE TO RELATED APPLICATIONS

This application claims priority to International Application Number PCT/US2019/033279, entitled "Single Cell Mapping and Transcriptome Analysis" filed May 21, 2019, which claims priority to U.S. Provisional Application No. 62/674,607, entitled "Single Cell Mapping and Transcriptome Analysis," filed on May 21, 2018, each of which is incorporated by reference herein in its entirety.

STATEMENT REGARDING FEDERALLY SPONSORED RESEARCH OR DEVELOPMENT

Not Applicable.

BACKGROUND OF THE INVENTION

Single cell analyses can provide a great deal of important information regarding cellular state and function. Single cell RNA sequencing (scRNA-Seq) enables the transcriptome of an individual cell to be profiled. Likewise, single cell proteomics can provide an accounting of cellular proteins, and single cell lipidomics enables characterization of membrane composition for individual cells.

While these remarkable tools provide great insight, tissue level effects on cellular function cannot be clearly elucidated with current methods. Cells work within a tissue microenvironment having higher-order organization and compartmentalization, wherein intra-tissue factors drive cellular responses. For example, factors such as the proximity of the cell to the tissue boundary, the architecture of the cell's surrounding extracellular matrix, and the proximity and identity of neighboring cells can have a profound effect on cell state. Unfortunately, these intra-tissue factors are largely a "black box" that cannot be readily resolved by current methods. Because single cell analyses such as scRNA-Seq require tissue dissociation into isolated cells, cell positional context is lost, and single cell analyses can only provide a bulk or population analysis of gene expression or other phenomenon within a tissue.

Accordingly, there is a need in the art to link tissue level contextual information with single cell properties, such as gene expression profiles.

SUMMARY OF THE INVENTION

Disclosed herein are novel inventions encompassing methods of analyzing single cells while preserving information about the position of the cell in a tissue or other complex multicellular structure. The various inventions encompass a mapping process for recording the spatial location of each cell within a tissue sample, which can be paired with single cell analysis techniques, such as single cell RNA sequencing, to map biological processes within the tissue.

By the methods of the invention, individual cells within a tissue section, cell culture, or other complex multicellular structure can be tagged with novel barcode constructs that denote the position of the individual cell in the larger structure. Subsequently, the individual cell is assayed, for example, a transcriptome analysis may be performed. By these novel inventions, the effects of the local environment surrounding a cell on its state and various functions can be elucidated, and intra-tissue processes can be mapped and observed. Likewise, coordinated actions by multiple cells within a tissue can be mapped and tracked over time.

In a first aspect, the scope of the invention encompasses a novel method of labeling single cells within a multicellular structure with positional information, and subsequently analyzing one or more parameters in the individual cells, wherein positional effects on the measured parameter(s) can be observed.

In one aspect, the scope of the invention encompasses a novel method of labeling cells within a multicellular structure with constructs that provide positional information, and subsequently performing single-cell analysis.

In one aspect, the scope of the invention encompasses novel constructs that may be utilized to label individual cells with positional information. In certain implementations, the constructs are oligonucleotide constructs.

In one aspect, the scope of the invention encompasses novel methods of combinatorial synthesis of unique tags that can be assigned positional information.

In one aspect, the scope of the invention encompasses novel systems comprising devices used in combination for performing the methods of the invention.

In one aspect, the scope of the invention encompasses novel methods of analyzing single cell state data, wherein positional information may be accounted for in the interpretation of such data.

In one aspect, the scope of the invention allows the user to select where and when to label cells with positional information, prior, during, and subsequent to any number of additional assays or treatments.

BRIEF DESCRIPTION OF THE DRAWINGS

FIGS. 2A, 2B, 2C, 2D, 2E, 2F, and 2G depict the illumination and additive syntheses scheme of four distinct zipcode tags in four spatially adjacent regions of multicellular sample.

FIG. 6B and depicts gene expression analysis of the B cell population showing differentially expressed genes between region 1 and region 2 localized cells. Vertical shading—Region 1, Diagonal shading—Region 2.

FIG. 9 depicts the illumination sequence for several populations of immune cells in order to define 4 distinct groups based on zipcode combinations.

DETAILED DESCRIPTION OF THE INVENTION

Figure 1A:
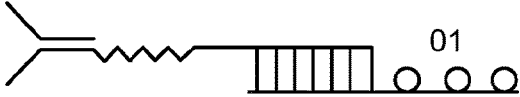
FIG. 1A depicts a foundation construct, comprising an anchoring moiety comprising an antibody to a cell surface moiety, a short generic double stranded oligonucleotide, and terminal single stranded overhang sequence 01, wherein the overhang sequence is protected by photolabile protection groups (circles).

The general method of the invention encompasses a process of labeling cells within a sample to preserve positional information, followed by one or more single cell analyses to measure parameters of interest. By the novel labels of the invention, the measured parameters can then be mapped across the tissue sample, elucidating positional and other microenvironmental factors that drive cell state.

In particular, the methods of the invention provide the art with a method to selectively label cells or tissues and in real time. By the methods of the invention, treatments can be applied to tissue or other samples, and the zipcoding can be applied 'after the fact', wherein users can choose where and when to add zipcode tags for maximum elucidation of effects. The methods of the invention enable users to optimize the timing, location, and investigative power of the measurements for maximum insight.

In a general implementation, the scope of the invention encompasses the following steps:

a sample comprising a multicellular structure is obtained;

a multitude of structurally and/or chemically unique constructs are applied to cells within the sample in a spatially defined manner, with each unique construct denoting a discreet physical position within the sample;

the sample is dissociated and a single cell analysis is performed wherein the cell's barcode is read and a selected cellular parameter is measured; and a profile of the measured parameter at various locations within the structure may be generated by means of the positional information.

The general operation of the method is referred to herein as the "zipcoding" of individual cells. A zipcoded cell is a cell to which one or more unique constructs have been applied, wherein the position of the cell within the sample at the time the tag is applied is recorded. As with postal ZIP Codes, which comprise a number of digits which may assume multiple values in a decimal code to denote a physical location, in some embodiments of the invention, the zipcode tags convey positional information by a binary code. Thus, positional information may be imparted to the cell while it is still within the multicellular structure. Subsequently, the multicellular structure is dissociated to facilitate measurement of one or more properties of the cell, and may be combined with positional data to derive insights about the effect of cell position on the measured property.

In a primary implementation of the invention, the unique constructs applied to cells in the multicellular structure are oligonucleotide constructs. These constructs may be readily synthesized by the methods disclosed herein to create unique zipcode tags at discrete sites within the sample. Following dissociation, the assembled zipcode tags present on each cell can be read by a single cell RNA sequencing process, providing data about cell state and position.

The various elements of the invention are described next.

Sample. The methods of the invention are performed on a sample. The sample may be any biological material comprising a multicellular structure. A preferred multicellular structure has at least one planar face, for example a tissue slice or section. Tissue sections are well known in the art and may be prepared by through vibratome sectioning or similar instrument. For example, tissue sections having a thickness of 10-10,000 microns may be used, for example, a tissue section of 100-1,000 microns, for example, a tissue section of about 300, 400, or 500 microns.

As the methods of the invention do not require a planar surface to be effective, in some embodiments, the sample is a tissue sample that does not have a substantially planar face. In some embodiments, the tissue is largely or entirely intact during the zipcode tagging process, and may assume a complex three dimensional geometry.

The tissue section may be derived from any suitable source. For example, the tissue section may comprise a tissue such as muscle, brain, kidney, pancreas, liver, lymphatic structure, or other organ or structure within the body. The tissue section may comprise a tumor or other neoplastic cells. The tissue section may be derived from an organism of any species, including, for example, animal species, plant species, fungal species, or other multicellular organisms. The animal species may be, for example, an invertebrate, a mammal, or a human.

In some embodiments, the sample comprises a tissue culture, for example, a planar tissue culture comprising confluent cells growing on a planar substrate or growth medium. In some embodiments, the cell culture comprises a single cell layer. In other embodiments, the cell culture comprises multiple cell layers. In some embodiments, the cell culture comprises an organoid culture. In some embodiments, the cell culture comprises synthetically aggregated cells, for example, cells in a printed tissue or cells infused within a three dimensional matrix.

In some embodiments, the sample to be analyzed comprises a conglomeration of single celled organisms, such as a biofilm or other multicellular culture or composition.

Zipcode Tags. In the methods of the invention, a zipcode tag or zipcode is applied to a cell. The zipcode tag will comprise a unique chemical species that can be "read" (identified) and distinguished from other zipcode tags applied to other cells. The zipcode tag may comprise any composition of matter that can be synthesized combinatorially.

In a primary implementation, the coding elements of the zipcode tag will comprise oligonucleotides. Oligonucleotides provide various advantages, including, for example, mature synthesis platforms, facile conjugation chemistry, facile reading by sequencing methods, and, in implementations wherein the single cell analysis is scRNA-Seq analysis, the integration of zipcode tag reading and cell analysis steps into a single step. Accordingly, the following description will be focused on the use of oligonucleotide zipcodes. However, it will be understood that the concepts of the invention may be extended to like zipcoding methodologies by means of other molecules, such as peptides, chemical species, and other compositions of matter.

The elements of an oligonucleotide zipcode tag are as follows.

Foundation Construct. Each zipcode oligonucleotide comprises a foundation construct. The foundation construct is a construct that serves two purposes. The foundation construct: (1) enables attachment of the zipcode tag to a cell; and (2) serves as a platform upon which a series of coding segments may be sequentially synthesized to create a unique zipcode tag.

A first element of the foundation construct is the anchoring moiety. The anchoring moiety is any composition of matter that will bind to or otherwise physically associate with a cell. The anchoring moiety may bind to, be adsorbed by, be absorbed by, or be integrated into the plasma membrane of the cell.

In one implementation, the anchoring moiety comprises a lipid that has affinity for the cell membrane. Exemplary lipid anchors include: phosphaditylethanolamine, phosphaditylethanolamine-caproylamine, azidocaproyl phosphaditylethanolamine, glycosylphosphatidyl-inisitol and cholesterol.

In one implementation, the anchoring moiety comprises an antibody. It is noted that reference to an "antibody" made herein will encompass intact antibodies as well as antigen-binding fragments thereof. The antibody may be selective for any cellular epitope or extracellular species, such as extracellular domains of membrane proteins or carbohydrate moieties. Exemplary antibodies include antibodies targeted to extracellular motifs of membrane proteins such as integrins, neural cell adhesion molecule, N-cadherin, E-cadherin, CD11a, CD27, CD40, CD46, CD95, CD45 aquaporin, ubiquitous membrane proteins such as glucose transporters GLUT1, and membrane ATPase.

In other embodiments, the anchoring moiety may comprise a membrane protein, an aptamer selective for extracellular motifs, or any other composition of matter that will bind to or otherwise physically associate with a cell.

In many implementations, it will be desirable to barcode every cell type in the sample, and the anchoring moiety will comprise a species that binds to most or all cell types, for example a lipid anchor. In other implementations, only a subset of cells within the tissue section are to be zipcoded and the anchoring moiety may comprise a species that selectively binds to specific cell types. Such selectivity may be imparted by the use of antibodies specific for differentially expressed membrane proteins. For example, if it was desired to tag only leukocytes, an anti-CD45 antibody could be utilized or CD31 could be utilized to selectively barcode lymph node stromal cells, etc.

Attached to the anchoring moiety is a base element. The base element is a moiety upon which the coding segments, described below, may be sequentially added. The base element may comprise any composition of matter upon which coding elements may be built. In the case of coding elements comprising oligonucleotides, the base element may comprise an oligonucleotide sequence. The anchoring moiety may be conjugated to the base oligonucleotide sequence by any appropriate chemistry known in the art. For example, thioether, amide, click chemistry groups, or thiol linkages between nucleic acids and peptide sequences, as known in the art, may be used to conjugate antibodies to the oligonucleotide portion of the anchoring construct.

The oligonucleotides used to synthesize the zipcode tags may comprise any type of nucleic acid, for example, DNA, RNA, PNA, or other natural or non-natural nucleic acid molecules known in the art. DNA is generally preferred for its stability and ease of use. Modification of the termini of these oligonucleotides with phosphorothioate bonds or other nuclease-resistant motifs can be included to increase resistance to degradation by nucleases that may be present in sample.

In some implementations, the foundation element may comprise an oligonucleotide sequence comprising a single stranded poly A strand.

Distal to the optional poly A chain, the foundation element may comprise a short double stranded nucleotide spacer sequence. The double stranded spacer sequence may comprise, for example, 5-50 nucleotides, 10-30 nucleotides, or about 15 nucleotides.

The base element will comprise a conjugation site upon which coding segments may be added. In the case of base elements comprising oligonucleotides, the conjugation site may comprise a terminal single stranded overhang. The single stranded overhang may comprise any sequence of oligonucleotides, for example a sequence of 3-20 nucleotides, 5-15 nucleotides, or about 10 nucleotides.

The conjugation site will be functionalized with protection groups. The protection groups block the conjugation site prevent the addition of coding segments until a deprotection stimulus is applied to remove the protection groups. Upon application of a deprotection step, the protection groups are cleaved, unbound, otherwise removed, or undergo a conformational change that results in the opening the conjugation site for hybridization to coding segments.

In a primary implementation, the protecting group comprises a photolabile chemical entity and the deprotection stimulus is light, specifically, light within a certain wavelength range and intensity sufficient to remove or degrade the photolabile species. Exemplary protecting groups include Black Hole Quencher (BHQ), nitrobenzyl, carbonyl, and benzyl-based protecting groups. Exemplary protecting groups include, for example, 3'-nitropheylpropyloxycarbonyl, and 2-(2-nitrophenyl)ethyl. Alternative DNA caging techniques may be utilized, such as the use of photo-isomerization of azobenzenes or photocleavable linkers in the DNA backbone.

Coding Segments. The methods of the invention encompass the use of a plurality of coding segments. The coding segments comprise chemically and/or structurally distinct segments that may be selectively combined to create a plurality of unique zipcode tags.

In a first implementation, the coding segments comprise "terminal strands," comprising an unprotected overhang sequence (e.g. 5' overhang) comprising a sequence which is complementary to the overhang sequence of the foundation construct, a double stranded coding sequence, a 3' polyadenine strand, and one or more fluorophores, as depicted in FIG. 1C-F. The function of the coding sequence element of the coding segment is to act as a unique identifier when the resulting zipcode tags are sequenced.

Figure 7A:
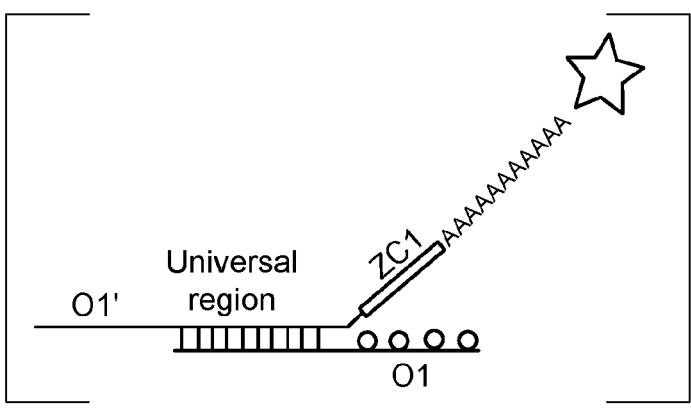
FIGS. 7A, 7B, and 7C depict branched zipcode coding segments having different coding sequences.
Figure 7B:
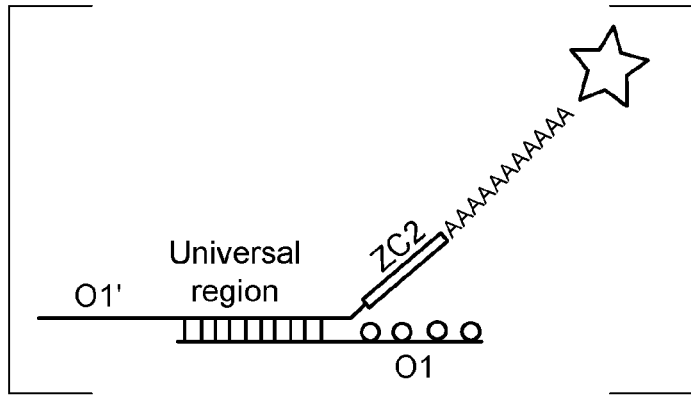
Figure 7C:
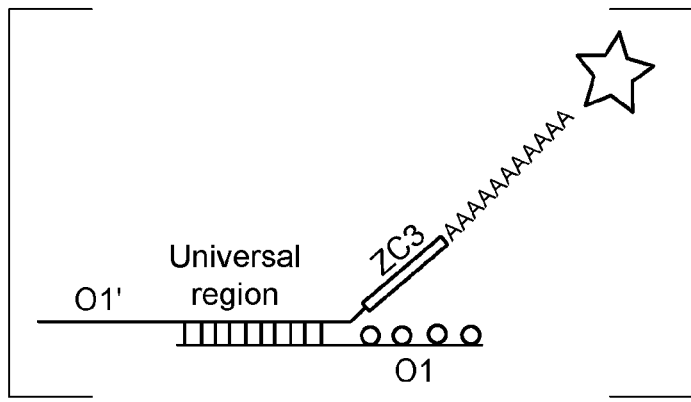

In an alternative implementation, a "branched" configuration for the coding segments is used. In this implementation, the coding segment comprises a first and a second strand, wherein the first strand comprises (for example, from 5' to 3') an unprotected overhang comprising a second overhang sequence which is complementary to the first overhang sequence of the foundation construct, a short spacer sequence that is hybridized to a complementary spacer sequence on the second strand, a coding sequence, a polyadenine tail, and one or more fluorophores, and wherein the second strand comprises a short spacer sequence hybridized to the complementary spacer sequence of the first strand, and an overhang (e.g. 5' overhang) comprising the first overhang sequence, wherein the overhang is functionalized with photolabile protection groups that inhibit hybridization of the overhang with complementary oligonucleotide sequences. Exemplary branched coding segments are depicted in FIG. 7A-C. Alternative configurations include alternative placement, or omission, of the fluorophore.

In a third implementation, the coding segments comprise "basic blocks" that are combined to create a single coding sequence that will act as the unique identifier for each cell. In this implementation, the coding segment comprises a double stranded oligonucleotide with both two overhangs of complementary sequences O1 and O1' (e.g. 5' overhangs) wherein one overhang (of sequence O1') is protected by photolabile or like protection groups. When provided to the sample, one the O1' overhang is protected, while the other overhang is able to hybridize to complementary O1 sequence overhangs on the base element and/or other coding elements, when such overhangs are deprotected by illumination, enabling the coding element to be selectively added to the zipcode element. Following the combination of coding segments in zipcode tags by hybridization of complementary overhangs, a ligase treatment is applied to create a continuous double stranded sequence.

In the coding segments of the invention, the coding sequence portion may comprise any length, however, a short sequence in the range of 5-50 nucleotides, for example 10-20 nucleotides is generally sufficient to impart a unique identifier and to avoid barcode cross-talk. The overhangs may comprise any length, for example, 3-15 nucleotides, for example, 5-10 nucleotides. Spacer sequences, if present, may comprise any length, for example, in the range of 3-20 nucleotides, for example 10-15 nucleotides.

The actual sequences used in the coding segments may be of any sequence. In general, inverted repeats and other sequences that form loops should be avoided to prevent interference with sequencing steps. In some implementations, it is preferred to use sequences that are not expected to be present in the cells of interest, to avoid confounding reads from native sequences present in the tagged cells.

In some implementations of the invention, every coding block comprises an adjacent 3' poly A strand. The inclusion of a poly A strand facilitates sequencing of the oligonucleotide zipcode tag by RNA-Seq methods. The poly-A chain comprises a sequence of adenine residues, the chain being at least of sufficient length to initiate sequencing in RNA-seq and like methodologies. For example, the poly A sequence may have a length of 5 to 100 adenines, for example, 10-50 adenines, 20-40 adenines, or about 30 adenines. It will be understood that the scope of the invention extends to any other construct that enables initiation of transcription or sequencing. For example, distinct capture sequences are utilized by sequencing platforms such as single cell sequencing by 10X Genomics, Inc. Such capture sequences may be incorporated into or conjugated to zipcode tags to facilitated sequencing by specific platforms, for example, in place of the poly A strand.

Fluorophores. In a preferred implementation, the zipcode tags of the invention will comprise a fluorophore. The inclusion of one or more fluorophores on the zipcode tag provides a means of selecting tagged cells from untagged cells following dissociation and during cell sorting. This enables efficient cell sorting and subsequent analysis, for example by RNA-seq. In a primary implementation, each coding segment comprises a fluorophore, for example, a fluorophore conjugated to the free end of the poly A strand. In an alternative embodiment, the fluorophore is present in the foundation construct.

The fluorophore may comprise any fluorescent or otherwise detectable composition. Exemplary fluorophores include dyes, fluorescent proteins, and other fluorescent moieties. Exemplary fluorophores include fluorescein and derivatives thereof, Alexa Fluor 488, AlexaFluor 647, Cy5, and TAMRA.

In one implementation, each unique zipcode tag coding sequence comprises a different fluorophore. Because each zipcode tag comprises a unique combination of the different coding segments, each will have a unique suite of fluorophores as well, and this will provide a distinguishable color that can be used to confirm or quantify the spatial application of the zipcode tags in the sample.

In some implementations, the zipcode tags may comprise one or more accessory moieties. The accessory moiety may comprise any chemical composition of matter. In some embodiments, the accessory moieties are conjugated to the ends of coding segment. For example, terminal moieties may be conjugated to the end of the poly A tail of a coding segment.

In some embodiments, the accessory moiety comprises an affinity tag, a conjugation partner for complementary compositions, or other such species, for example, biotin, for example, to facilitate purification of tagged cells.

In other embodiments, the accessory molecule is a biologically active molecule which acts upon the cell to which it is conjugated, for example, an enzyme, receptor ligand, receptor inhibitor, or other molecule (e.g. a protein or drug).

In some embodiments, the accessory moiety is protected by a photolabile or similar protection group, such that selective illumination is required to activate or enable the action of the accessory molecule.

Zipcode Tagging Systems. The scope of the invention encompasses various systems for the application of zipcode tags to samples. The systems may comprise a number of devices in combination. In a general implementation, the system comprises a sample substrate upon which the sample is placed;

a microscopy system for imaging the sample;

a microfluidic chamber encasing the sample, wherein the microfluidic chamber is in connection with a plurality of reservoirs, wherein a first reservoir will contain a buffer solution for washing steps; a second reservoir will comprise a solution comprising a foundation construct; and a plurality of additional reservoirs wherein each contains a solution comprising a unique coding segment; and pumping means and suitable control systems for selectively introducing each of the solutions to the microfluidic chamber, and pumping solutions out of the chamber to a waste collection vessel;

an illumination system for selectively delivering light energy to selected sites in the sample, the light being of sufficient energy to cleave photolabile protection groups;

an X-Y staging system that enables movement of the sample within the field of view of the microscope, and which allows for selective illumination at precisely defined points by the illumination source; and computer control elements for coordinating the activity of the components.

A first component of the zipcode tagging system is the sample chamber. The sample chamber provides a substrate upon which the sample is placed and wherein tags are applied to the sample. The sample substrate may comprise any suitable planar surface upon which samples can be placed. For example, systems known in the art for the immobilization of tissue sections or slides may be used.

The zipcode tagging system will further comprise a microscope. The sample chamber will be configured such that the entire sample area can be viewed by the microscopy system. Any microscopy system may be employed that enables a user to image the sample and identify regions of interest for application of zipcode tags. Exemplary microscopy systems include wide-field, 2P and confocal imaging systems, as known in the art. The microscopy system enables the user to image the sample and to direct the application of zipcode tags to selected points or sectors of the sample. Imaging of samples structures may aided by the use of stains such as immunotoxins or immunofluorescence to delineate various regions or structures within the sample. For example, 2P morphological analysis of the sample may be performed to identify tissue compartments, characterize extracellular matrix architecture, and image other tissue features such as local density of certain cell types, cell morphologies, and proximity to tissue structures. Likewise, by immunofluorescent indicators, a functional analysis of the sample may be performed to identify sites of biological activity, cell-cell interactions, and signaling activities.

The microscope may serve both to visualize particular features of the multicellular sample and also to provide the spatial a means of delivering light to specific regions of the sample. Elements of the microscopy system may be components of the selective illumination system described below.

The sample chamber may also comprise a microfluidic chamber. The microfluidic chamber comprises a watertight vessel that will encase the sample and which will be in connection with a plurality of reservoirs. A first reservoir will contain a buffer solution for washing steps. A second reservoir will comprise a solution comprising the foundation construct. A plurality of additional reservoirs will each contain a solution comprising a unique coding element. The system will further comprise pumping means and suitable control systems for selectively introducing each of the solutions to the microfluidic chamber, such that the cells of the sample are exposed to the selected solution. The device will further be capable of pumping solutions out of the chamber to a waste collection vessel.

The microfluidics chamber may comprise a top surface that is substantially transparent, for example, comprising glass, polycarbonate, PDMS or other materials that are transmissive of light energy and which enable viewing from above, below, or another angle, by microscopy. In alternative implementations, the top is open.

The systems of the invention will further comprise a selective illumination system. The selective illumination system will comprise an energy source, e.g. a light source, capable of delivering a deprotection stimulus to the surface of the sample. For example, in one embodiment, the energy source comprises a laser, for example a UV laser or a mercury arc lamp. The energy source will be integrated with a selective focusing system, which enables the controlled delivery of the light or other energy to selected sectors of the sample. For example, the selective illumination system may comprise a digital micromirror device, for example, such as devices described in PCT International Patent Application Publication Number WO2003065038, entitled "Apparatus for synthesis or arrays of dna probes using micromirrors, prism and kaleidoscopic element," by Cerrina and Huang and United States Patent Application Publication Number 20100255426, entitled "Mirror arrays for maskless photolithography and image display," by Jain et al. In some implementations, a masking system is used in combination with a light source to achieve selective illumination.

The system of the invention will comprise an X-Y staging system that enables movement of the sample within the field of view of the microscope, and which allows for selective illumination at precisely defined points by the illumination source. The X-Y staging system may be integral to the sample substrate, enabling its movement under the microscope and illumination systems. Alternatively, the X-Y staging system may be integrated into the microscopy and selective illumination devices, enabling their movement and precise placement over the sample.

The sample chamber may optionally comprise heating and/or cooling elements and suitable temperature controls for maintaining the sample at a desired temperature, for example physiological temperatures (e.g. about 37° C.) or a cooled environment (e.g. about 4° C.) to help preserve samples in their native state prior to being sampled.

The systems of the invention will also comprise one or more computer control elements for coordinating the activity of the components. For example, the computer system will comprise a means for outputting an image of the sample to a user, wherein the user may select points, transects, or planar sectors where the application of zipcode tags is desired. By an interface, such as a mouse, pen, or other such tool, the user may delineate those areas of the sample where zipcoding is desired. The computer control system will be configured to determine the number of zipcode tags to be synthesized, and to develop a synthesis scheme for the creation of the required number of unique zipcode tags. Programs known in the art, for example METAMORPH™ (Molecular Devices, LLC) and microManager (Open Imaging Inc.). The computer system will be in functional connection with the microfluidics and selective illumination components to carry out the synthesis scheme by a series of illumination, coding segment application, and wash steps, as described below. The computer control system will further comprise memory for storing positional information associated with zipcode tag sequence information.

The computer control system may comprise software and a storage medium on which such software is stored, distributed, and read. In one embodiment, the invention comprises a non-transitory computer-readable recording media having stored thereon an encoding program that causes a computer to execute a process, the process comprising one or more operations set forth in the methods of the invention.

Zipcode Tagging Process. The methods of the invention are directed to the synthesis of a set of unique zipcode tags on cells at a plurality of selected sites within a sample. Each unique zipcode will be associated with a known, specific site (location) within the sample. The general process of synthesizing zipcode tags on cells is as follows:

the sample is exposed to a solution comprising a foundation construct comprising an anchoring moiety and a protected overhang sequence;

the sample and foundation incubate for a period of time sufficient for the anchoring moieties of the foundation constructs to bind to cells in the sample;

a synthesis process is performed, comprising the steps of:

selectively illuminating one or more of the selected sites with an energy source that removes photolabile protection groups;

exposing the sample to a solution comprising a selected coding segment, wherein overhang sequences of the coding segment will hybridize to complementary overhang sequences that have been deprotected by illumination;

applying a wash step to remove unbound coding elements; and repeating the synthesis process with the use of coding segments comprising unique coding sequences in each cycle.

By this method, cells can be tagged with zipcode constructs comprising unique identifiers, wherein each identifier is associated with a specific site in the sample, such that, when the sample is subsequently dissociated and single cells are analyzed, each tagged cell's position in the sample prior to dissociation can be determined.

The zipcode tag synthesis process will vary depending on the type of coding segments used. In the case of terminal coding segments, for example, as depicted in FIG. 1C-1F, the zipcode tag synthesis and reading process is carried out as follows:

exposing the sample to a solution comprising a foundation construct comprising an anchoring moiety and an oligonucleotide sequence comprising an overhang, wherein the overhang is functionalized with photolabile protection groups that inhibit hybridization of the overhang with complementary oligonucleotide sequences;

allowing the sample and foundation construct to incubate for a period of time sufficient for the anchoring moieties of the foundation constructs to bind to cells in the sample;

illuminating one or more selected sites in the sample with an energy source that cleaves photolabile protection groups present in the one or more sites;

exposing the sample to a solution comprising a coding segment, the coding segment comprising an unprotected overhang sequence comprising a sequence which is complementary to the overhang sequence of the foundation construct, a double stranded coding sequence, a polyadenine strand, and one or more fluorophores;

applying a wash step to remove unbound coding segments; and repeating one or more times the cycle of the previous three steps with the illumination of one or more unique sites in each cycle and the use of coding segments comprising unique coding sequences in each cycle;

dissociating the sample to single cells; and performing a single cell transcriptome analysis of the dissociated cells wherein, for each cell, the transcriptome of the cell is characterized and, if present, the sequence of one or more unique coding sequences applied to the cell in the preceding steps is read, wherein each unique coding sequence is associated with a position in the sample such that the cell's position in the sample prior to dissociation can be determined.

The use of terminal tags requires a unique coding segment for each unique of zipcode tag to be synthesized.

The use of branched coding segments enables a more combinatorial approach. In the case of branched coding segments, the synthesis of zipcode tags and reading of the coding sequences is as follows:

exposing the sample to a solution comprising a foundation construct comprising an anchoring moiety and an oligonucleotide sequence comprising an overhang comprising a first overhang sequence, wherein the overhang is functionalized with photolabile protection groups that inhibit hybridization of the overhang with complementary oligonucleotide sequences;

allowing the sample and foundation construct to incubate for a period of time sufficient for the anchoring moieties of the foundation constructs to bind to cells in the sample;

illuminating one or more selected sites in the sample with an energy source that cleaves photolabile protection groups present in the one or more sites;

exposing the sample to a solution comprising a coding segment, the coding segment comprising an oligonucleotide comprising a first and a second strand, wherein the first strand comprises an unprotected overhang comprising a second overhang sequence which is complementary to the first overhang sequence, a short spacer sequence that is hybridized to a complementary spacer sequence on the second strand, a coding sequence, a polyadenine tail, and one or more fluorophores, and wherein the second strand comprises a short spacer sequence hybridized to the complementary spacer sequence of the first strand, and an overhang comprising the first overhang sequence, wherein the overhang is functionalized with photolabile protection groups that inhibit hybridization of the overhang with complementary oligonucleotide sequences;

applying a wash step to remove unhybridized coding segments; and repeating one or more times the cycle of the previous three steps with the use of coding segments comprising unique coding sequences in each cycle;

dissociating the sample to single cells; and performing a single cell transcriptome analysis of the dissociated cells wherein, for each cell, the transcriptome of the cell is characterized and, if present, the sequence of one or more unique coding sequences applied to the cell in the preceding steps is read, wherein the specific combination of coding sequences present is associated with a position in the sample such that the cell's position in the sample prior to dissociation can be determined.

Figures 7D, 7E:
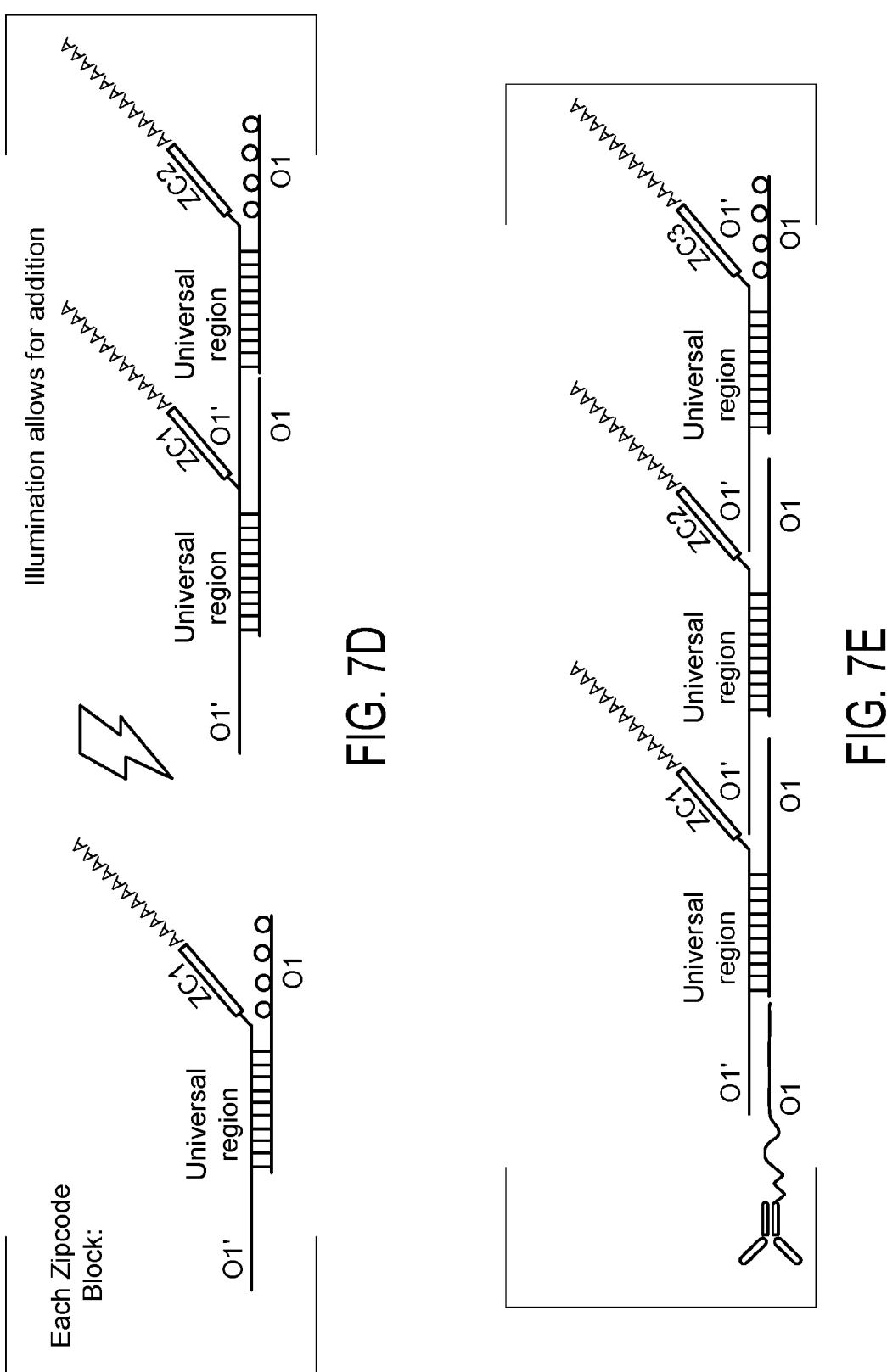
FIG. 7D depicts the addition of second block on a first block.
FIG. 7E depicts a zipcode tag comprising the three branched zipcode coding segments of FIGS. 7A, 7B, and 7C hybridized to an anchoring construct.
Figure 7F:
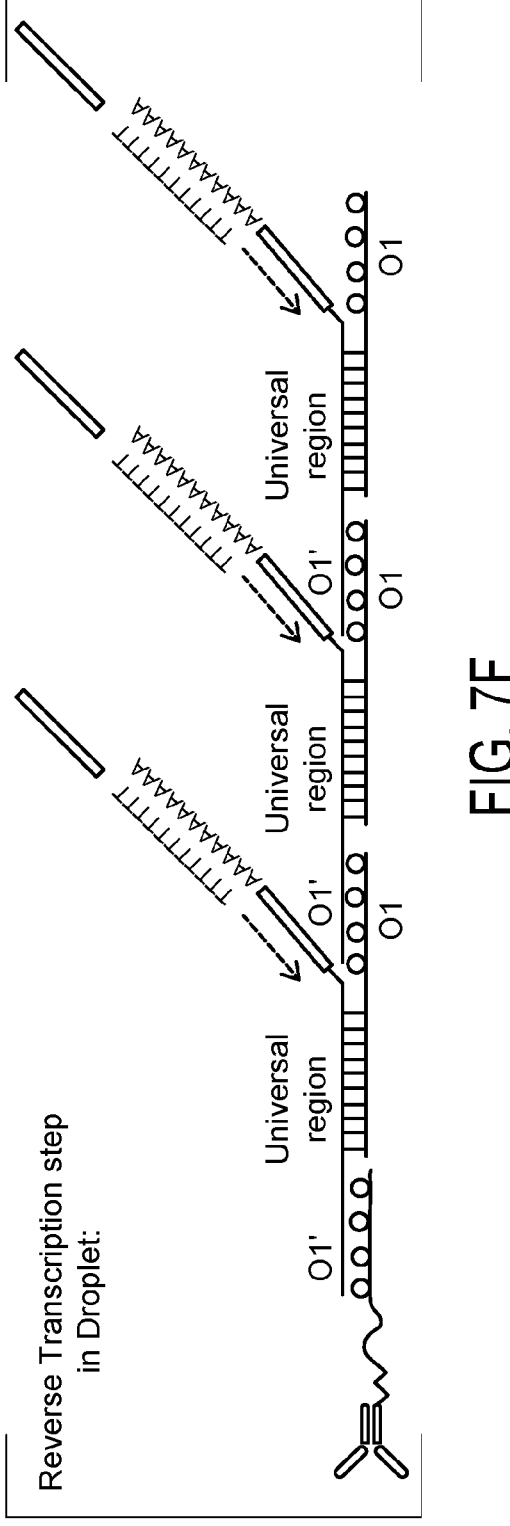
FIG. 7F depicts how these three branched zipcode segments are captured by reverse transcription in droplets during scRNA-Seq protocols. Circles depict photolabile protection groups. Stars depict fluorophores.

The synthesis of a zipcode tags comprising branched coding segments is depicted in FIGS. 7D and 7E. By combinatorial synthesis, a zipcode tag comprising a chain of branched coding blocks may be assembled. The poly A tail of each block provides an initiation site for RNA sequencing such that will be separately read, resulting in a readout of each distinct coding sequence that has been incorporated into the zipcode tag. For each distinct zipcode tag sequence that is utilized, it can be either present or absent in the resulting zipcode tag construct. Thus, for x number of distinct coding sequences used, the number of distinct zipcode tag combinations is $2^x$. For example, by the use of 10 distinct coding sequences, 1,024 distinct zipcode combinations can be synthesized. With twenty distinct coding sequences, 1,048,576 distinct zipcode combinations can be present.

In a third variation of the process, basic block coding segments are utilized. In this variation of the process, synthesis of zipcode tags and reading of the coding sequences is as follows:

exposing the sample to a solution comprising a foundation construct comprising an anchoring moiety and an oligonucleotide sequence comprising an overhang comprising a first overhang sequence, wherein the overhang is functionalized with photolabile protection groups that inhibit hybridization of the overhang with complementary oligonucleotide sequences;

allowing the sample and foundation construct to incubate for a period of time sufficient for the anchoring moieties of the foundation constructs to bind to cells in the sample;

illuminating one or more selected sites in the sample with an energy source that cleaves photolabile protection groups present in the one or more sites;

exposing the sample to a solution comprising a coding segment, the coding segment comprising an oligonucleotide comprising a first unprotected overhang comprising the first overhang sequence, a double stranded coding sequence, and a second overhang comprising a second overhang sequence complementary to the first overhang sequence, wherein the second overhang is protected by photolabile or like protection groups;

applying a wash step to remove unhybridized coding segments; and repeating one or more times the cycle of the previous three steps with the use of coding segments comprising unique coding sequences in each cycle;

applying a terminal oligonucleotide comprising a polyadenine strand to all zipcode tags in the sample; and applying a ligase treatment to join hybridized coding segments, the foundation construct, and the terminal oligonucleotide into a continuous double stranded sequence;

dissociating the sample to single cells; and performing a single cell transcriptome analysis of the dissociated cells wherein, for each cell, the transcriptome of the cell is characterized and, if present, the continuous sequence created by the ligation of the coding segments is read, wherein the specific ordering of coding sequences is associated with a position in the sample such that the cell's position in the sample prior to dissociation can be determined.

In the ligation step, any treatment that facilitates ligation of hybridized oligonucleotides may be applied. For example, a solution comprising DNA ligase may be applied to the sample under conditions favorable for the ligation of hybridized overhangs. Chemical ligation treatments may be applied in place of enzymatic ligation.

In a variation of the method, the poly A sequence is present in the foundation construct, in addition to or instead of being applied as a terminal oligonucleotide block comprising a poly A sequence.

By use of basic block coding segments and ligation to create continuous strands, a zipcode tag sequence may be synthesized fully combinatorially. In this implementation, the ordering, number, and presence of specific coding sequences provides diversity to the zipcode tag identifiers. Therefore, the number of potential zipcode tag sequences scales exponentially with the number of unique coding segments used and the number of hybridization steps performed. For example, using four distinct coding segments and eight hybridization steps, 65,536 unique zipcode tag sequences may be generated.

In the methods of the invention, the synthesis of the zipcode blocks may be controlled by a computer program which determines the number of coding segments and hybridization steps necessary to tag the selected area, formulates the composition of each zipcode construct the sequence of hybridizations steps, assigns a unique zipcode tag composition to a specific site in the sample and stores this data for later analysis, and which controls the operations of the microfluidics to synthesize the zipcode tags.

In a variation of the various zipcode tag synthesis methods describe above, one or more intervening adapter sequences may be employed. The adapter sequences will be configured as in FIG. 1B, comprising an unprotected overhang, a short double stranded spacer, and a second protected overhang. By varying the sequences of the overhang and configuring sets of coding segments to have complementary overhangs, the adapter sequence provides orthogonal coding segments that can be combined in single hybridization steps. This can be used to reduce the number of hybridization cycles. An example of zipcode tag synthesis using an adapter sequence is described in Example 1.

In the various zipcode tag synthesis methods of the invention, the wash steps may comprise the use of physiologically compatible buffer or medium. In some embodiments, the solution applied in the wash step comprises blocking strands complementary to overhang sequences of the previous wash step, in order to bind and neutralize any unbound oligonucleotide from the previous step to prevent carry-over.

In the synthesis of zipcode tags, the size of the illumination sites is determined by the resolution of the selective illumination focusing system. In some implementations, the illuminated sector size will exceed average cell size, such that multiple cells are present within an illuminated sector. In some implementations, the illuminated sector size is less than the average cell size, such that each cell receives one or more unique zipcode tags. In a preferred implementation, the sector size is about equivalent to that of average cell size, such that each cell receives a predominant single unique zipcode tag (e.g. a single type of zipcode tag makes up greater than 50%, greater than 60%, greater than 70%, greater than 80%, or greater than 90% of the zipcode tags applied. For example, selective illumination systems are capable of illuminating spot sizes in the range of 500 nanometers, while most cells are sized about 10 microns.

The selection of the sites may be determined by the user. In one embodiment, sites are arranged in a grid or sector that covers all or a portion of the sample, such that every cell in the planar surface of the sample may be positionally tagged. In an exemplary implementation, the selected sites comprise a grid of square having a size of 5 by 5 microns. In alternative embodiments, the sites are arranged in a line or transect, for example, to study the effects of distance from a feature of interest. In another implementation, the sites are distributed in a discontinuous or irregular manner, wherein features of interest distributed throughout the sample can be selectively tagged.

In a primary implementation, every site that is labeled with a zipcode tag receives a unique combination of coding sequences. In an alternative implementation, multiple sites are labeled with the same zipcode tag sequence. For example, a user may select two different cell types within a sample, a and b, and apply the two zipcode tags A and B, to the cells of each type. This allows the use to survey multiple cell or region types throughout the sample with a low number of coding segments and synthesis steps.

Advantageously, the methods of the invention enable users to perform any number of assays prior to or concurrently with the zipcoding process. For example, the tissue or other sample may be subjected to modification and/or treatments that result in the expression of reporter constructs or other measurable signals. The user may select particular sites of biological activity for zipcode tag application, for example, as evidenced by fluorescent signals viewed via microscopy. The real time ability to tag subpopulations of cells in selected states enables acquisition of data that is not possible in bulk labeling methods or methods that require simultaneous labeling of all cells. In one implementation, the methods of the invention are applied in cell motility assays, wherein zipcode tags are applied to moving cells.

An advantage of the methods disclosed herein is that they may be applied not just to cells at the surface of the sample, but to cells within the sample. By visualization modes such as 2P microscopy, tissues may be visualized to large depths (e.g. 1 mm). Oligonucleotide building blocks of the zipcode tags will typically penetrate several cell layers deep into tissue samples. Furthermore, penetration depth capacity of the oligonucleotides and delivery solutions can be tuned by methods known in the art, for example by the use of oligonucleotides conjugated or complexed with cell penetrating peptides such as TAT and penatratin. Combined with selective illumination capabilities, specific cells or ranges of cells within the column may be selected for synthesis of zipcode tags.

Zipcode Reading and Single Cell Analysis. Following the zipcode tagging process, the sample is next subjected to a dissociation treatment to isolate individual cells. Any dissociation treatment known in the art may be applied, for example by enzymatic, mechanical, or combined methods. For example, enzymatic treatments by trypsin, collagenase, or hyaluronidase may be utilized. A cell suspension is produced from the dissociated sample.

Individual cells from the dissociated sample may be isolated by means known in the art, for example, flow cytometry, fluorescence activated cell sorting, digital dielectrophoretic sorting, magnetic capture and other methods known in the art.

The cells of the cell suspension are then subjected to one or more single cell analyses.

In a primary implementation, the single cell analysis comprises a transcriptome analysis. Single cell RNA sequencing (scRNA-Seq) enables measurement of the gene expression profiles in each tagged cell. Advantageously, zipcode tag reading and transcriptome analysis may advantageously be accomplished in a single step. Single Cell RNA sequencing methodologies that make use of polyA capture for cell-specific labeling of cDNA will also capture the polyA chains on the applied zipcode tags, allowing these zipcode tag sequence reads to be incorporated into traditional RNA Seq workflow as an orthogonal library to the cDNA library. Reading of the zipcode tag enables the cell's position in the sample to be determined by checking against the stored location of the specified sequence.

In some cases, a cell will be found to have two or more types of zipcode tag. For example, a cell at the boundary of two illumination sites may have tags from both. In such cases, positional information can be derived by the application of suitable statistical methodologies to resolve the likely location of the cell in the sample.

scRNA-Seq may be accomplished by any number of methodologies known in the art, for example, by SMARTseq2, MARS-seq, CELL-seq and Drop-sect methodologies, as known in the art. Exemplary commercial platforms include Fluidigm C1™ (Fluidigm Corporation, USA), Wafergen ICELL8™ (Wafergen hiosystenis, Inc., LISA) and the lox Genomics Chromium™ (10X Genomics, Inc., USA).

In addition to RNA-seq for transcriptome analysis and zipcode tag reading, the individual cells recovered from the sample may be subjected to additional assays, for example, single-cell analyses, detection of specific proteins or other species by immunostaining, or any other assay, survey, or characterization of the cell. Exemplary single cell analyses include, for example, single cell proteomic analysis, single cell lipidomic analysis, whole genome amplification and sequencing, single cell metabolomics analysis, and other assays of cell state.

In a final step, the results of the zipcode tag reading and the one or more single cell analyses are utilized to reconstruct the spatial distribution of a selected parameter of interest in the sample. Using the known distribution of the zipcode tags across the sample, the parameters measured for each cell in the one or more analyses may be mapped to the position of the cell within the sample prior to dissociation. Accordingly, the distribution of the measured parameter(s) within the tissue may be visualized and correlated to factors such as the identity and abundance of neighboring cells, proximity to tissue borders, extracellular matrix architecture, and other factors. This data may be overlaid with microscopy data acquired prior to tissue dissociation to provide further context for the measured parameters. Such reconstruction may be applied to multiple adjacent tissue sections derived from a sample in order to create a three dimensional map of the measured parameter across a volume of tissue. By these methods, a comprehensive profile of various cell states, processes, or properties may be mapped across a tissue, revealing tissue-scale processes and local micro-environmental effects on cell behavior and state.

Oligonucleotide Tag Synthesis Kits. In one aspect, the scope of the invention encompasses kits for facilitating the methods of the invention. In one embodiment, the kits of the invention comprise a collection of two or more coding segments. The kit will comprise the two or more coding segments wherein each such coding segment is packaged in its own container, and the containers are packaged in a common packaging unit. For example, the coding segments may be in solution or lyophilized powder form and may be in containers comprising vials, bottles, envelopes, and other suitable packing materials. The two or more containers will then be packaged in a common packaging element, for example, a box or cannister.

In one embodiment, the kits of the invention comprise two or more coding segments comprising terminal segments. In one embodiment, the kits of the invention comprise two or more coding segments comprising branched coding segments. In one embodiment, the kit comprises two or more coding segments comprising building block coding segments. In one embodiment, the kits comprise an additional container comprising a foundation construct. In one embodiment, additional components such as buffers and/or other components utilized in hybridization reactions. The kit may comprise any number of coding segments, for example, at least four, at least ten, or at least unique coding sequences.

EXAMPLES

Example 1. Controlled Hybridization of Oligonucleotides on Live Cells

Figure 1B:
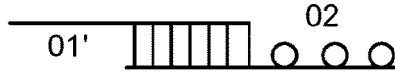
FIG. 1B depicts a "second layer" adapter construct, comprising an unprotected overhang comprising a sequence denoted O1', which is complementary to overhang sequence 01. The opposite end of the adapter construct comprised a protected overhang sequence 02.
Figure 1C:
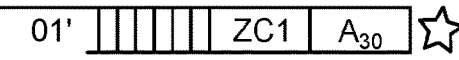
FIGS. 1C, 1D, 1E, and 1F depicts a coding segments comprising single stranded overhangs complementary to sequences 01 or 02, and comprising different double stranded coding sequences, ZC1, ZC2, ZC3, and ZC4. Each coding segment also comprised a terminal poly A tail of 30 adenines. The circles depict photolabile protection groups and the stars depict fluorophores.
Figure 1D:
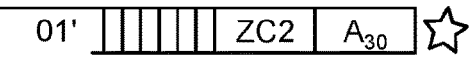
Figure 1E:
Figure 1F:

A monolayer of primary murine T cells was plated in growth medium. A foundation construct (FC) as depicted in FIG. 1A was synthesized comprising an antibody to cell surface marker CD45 was, a short generic double stranded oligonucleotide, and terminal single stranded overhang of sequence denoted O1, protected by photolabile protection groups comprising NPOM. A "second layer" adapter construct (SL), as depicted in FIG. 1B was also synthesized, comprising an unprotected overhang comprising a sequence denoted O1', which is complementary to overhang sequence 01. The opposite end of the adapter construct comprised a protected overhang sequence 02. Coding segments Z1, Z2, Z3, and Z4, as depicted in FIGS. 1C, 1D, 1E, and 1F respectively, were also synthesized, comprising single stranded overhangs complementary to sequences 01 or 02, and comprising different double stranded coding sequences, ZC1, ZC2, ZC3, and ZC4. Each coding segment also comprised a terminal poly A tail of 30 adenines.

FIG. 2A-2G depict the syntheses scheme of four distinct zipcode tags in four spatially adjacent regions of the murine cell culture. Cells were first exposed to a solution of the foundation construct, wherein the antibody anchoring moiety resulted in binding to the cell surface of the foundation construct in all sectors (FIG. 2A). The top two sectors were illuminated (shading in FIG. 2B), followed by exposure of a solution comprising the second layer adapter construct SL, resulting in addition of the adapter construct in the previously illuminated sectors (FIG. 2C). Next, the left hand blocks were illuminated (shading, FIG. 2D), followed by exposure of the cells to a solution comprising constructs Z1 and Z3, resulting in the addition of each to complementary overhangs in the previously illuminated sectors (FIG. 2E). Next, the right hand blocks were illuminated (shading, FIG. 2F), followed by exposure of the cells to a solution comprising constructs Z2 and Z4, resulting in the addition of each to complementary overhangs in the previously illuminated sectors (FIG. 2G). The result was four discrete sector comprising four distinct zipcode tag sequences.

FIG. 3A-3D depicts a synthesis scheme using two different oligonucleotide sequences comprising two different fluorophores. By sequential selective illumination and hybridization, four distinct sectors comprising oligonucleotide sequences comprising a first fluorophore, a second fluorophore, both fluorophores, and neither fluorophore were synthesized. When imaged by fluorescent microscopy, fluorescent signal from each sector was visually distinct (represented by different shading in the four sectors of FIG. 3D). This demonstrated efficient, highly binary, combinatorial and spatially controlled synthesis of zipcode tags in adjacent sectors.

Figures 3A, 3B, 3C, 3D, 4:
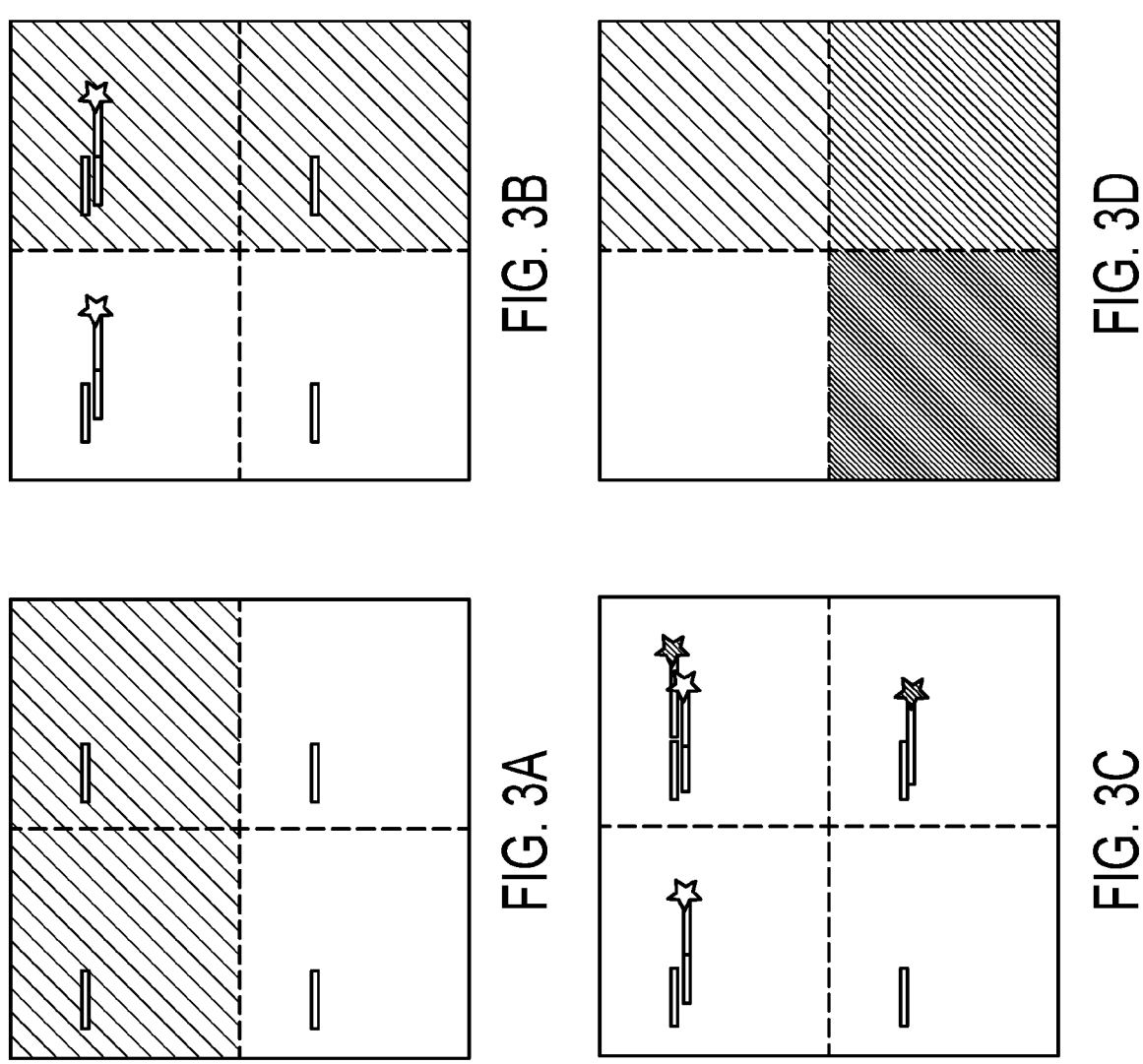
FIG. 3A-3D depicts a synthesis scheme using two different oligonucleotide sequences comprising two different fluorophores which generates 4 regions with distinct fluorophore combinations.
FIG. 4 depicts the illumination sequence for different sets of distinct murine primary cell types in order to specify 2 populations defined by either zipcode 1 or 2

In order to test the ability of zipcode sequences to be read out by 10X sequencing, several distinct murine primary cell types were subjected to varying patterns of light illumination (FIG. 4). This pattern resulted in CD4 T and dendritic cells receiving a zipcode tag comprising coding sequence ZC1 and CD8 T and macrophages receiving a zipcode tag comprising coding sequence ZC2. RNA sequencing by 10X sequencing platform was performed and two sharply defined populations with either zipcode tag dominated the read counts. When zipcode identity was plotted on transcriptional space (tSNE plot), a strong correlation between transcriptional identity and zipcode identity was observed, demonstrating that the zipcode tag strategy can link transcriptomes to distinct regions defined by the user.

Example 2. Detecting Distinct Transcriptional Programs in a Wound Healing Model The zipcode tags of the invention were applied to a cultured monolayer of fibroblasts. Murine NIH3T3 fibroblasts were seeded on growth medium and allowed to grow to confluency. The monolayer was then 'wounded' using a pipette tip 12 hours prior to imaging and cell labeling. A foundation construct comprising a photocaged overhang strand and intercalating lipid was applied to the cell cultures. After imaging the wound edge in bright field, two regions were selected of 150 micron width. The regions, Region 1 and Region 2 were 0-2000 and 2000-400 um from the leading edge of cells, respectively. Each region was illuminated in a spatially defined manner using 800 ms pulses of 360 nm UV light from a Mercury arc lamp. After illumination of the first region, construct Z1 (FIG. 1C) was pipetted onto the cultured cells. After a 5 minute incubation to allow for hybridization, the oligo solution was removed and the cells were, washed with 200 uL of pre-warmed RPMI 3 times to remove unbound oligo. In order to ensure that residual zipcode 1 did not bind uncaged strands during the second round, a blocking strand, complementary to the hybridization region of the Z1 was applied to neutralize unbound Z1 construct. This process was repeated for Region 2 located 150-300 microns further in from the wound site, using a second, distinct zipcode tag sequence. Cells were then washed and blocked again. They were then briefly incubated with Accutase at RT for 5 min to detach and dissociate, washed in PBS+0.04% BSA, then brought up to a concentration of 1e6/mL before proceeding to 10X encapsulation following standard protocol.

Cells were run using the 10X v2 3' Chemistry. Library construction steps were slightly altered to allow for generation of two libraries in parallel, the cDNA and the Zipcode libraries. After qPCR quantification the ZC and cDNA were mixed at a 1:10 molar ratio and sequenced on two lanes of an Illumina HiSeq. Using 10X bcl2fastq, the ZC library was demultiplexed from the cDNA library. Zipcodes were counted for valid cell barcodes in order to determine which region the cells derived from.

Figure 5A:
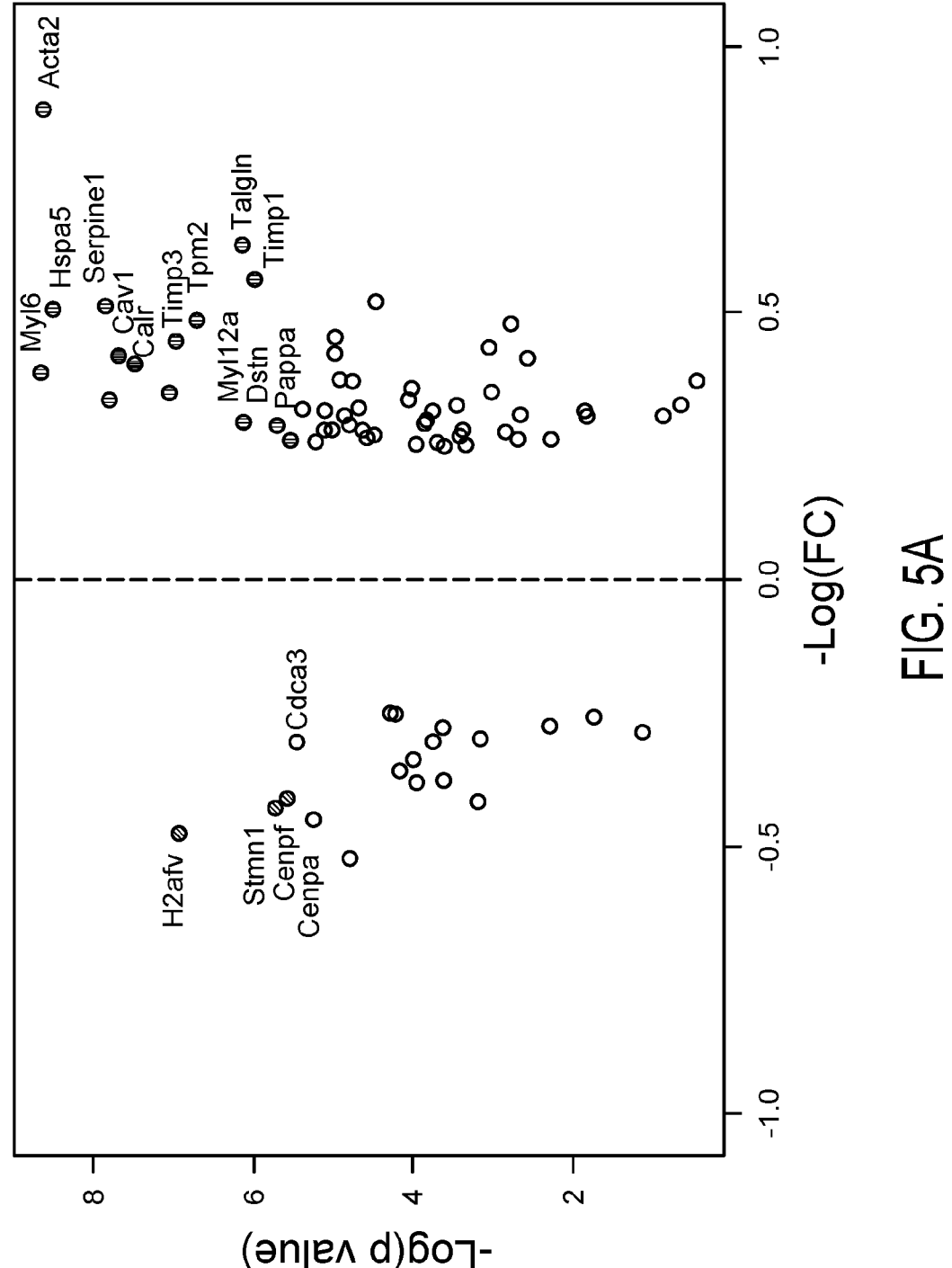
FIG. 5A depicts gene expression plot of cells tagged in two regions of a cell culture wound healing model, diagonal shading, Region 2 cells, vertical shading Region 1 cells.
Figure 5B:
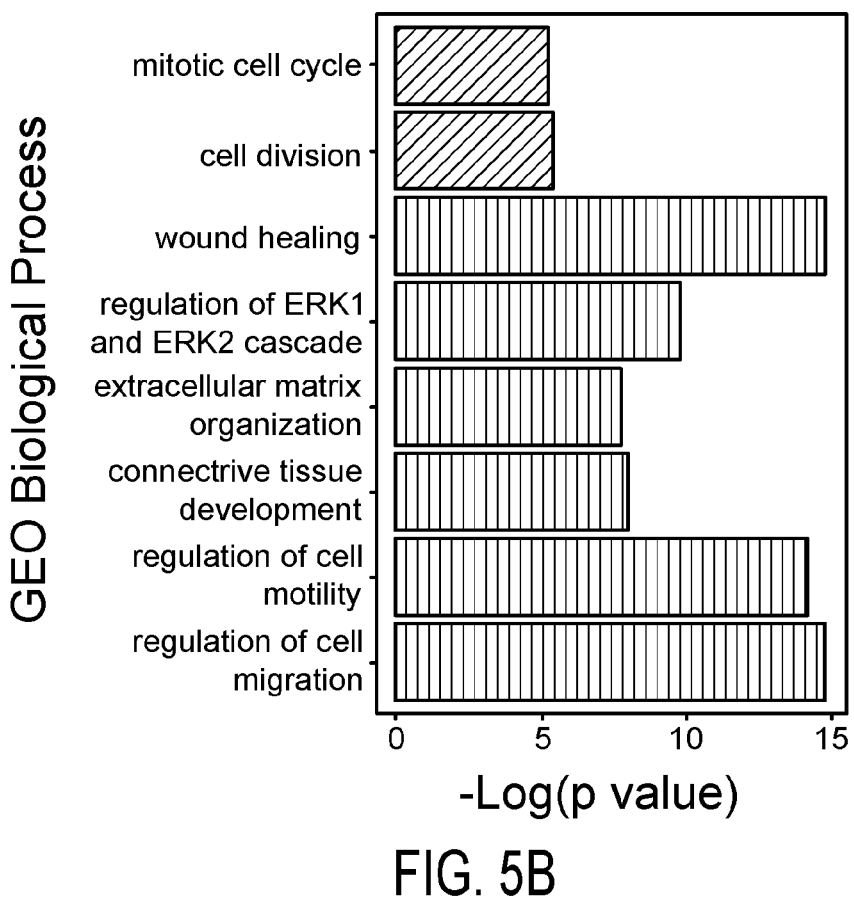
FIG. 5B depicts gene ontology analysis results wherein, genes enhanced in region 1 include ECM organization and cell motility genes while processes in region 2 include cell cycle and cell division.

Transcriptional data was analyzed using the R package Seurat which revealed the transcriptional heterogeneity within the population. Overlaying regional identity onto transcriptional data revealed concentration of Region 1 and 2 cells into distinct clusters. Focusing on only labelled cells, differential expression analysis revealed a number of genes preferentially expressed in cells based on region. For example, cells proximal to wound edge (Region 1) show enhanced expression of genes involved in cytoskeletal activity (e.g. Acta2, My19, Tagln) and ECM remodeling (e.g. TIMP, Serpine, Hspa5). Meanwhile cells more distal to the wound edge from Region 2 displayed enhanced expression of genes related to cell cycle such as Cenpa, Cenpf, H2afv (FIG. 5A). Indeed when the gene lists are passed through gene ontology analysis, enriched processes in region 1 include ECM organization and cell motility while processes in region 2 include cell cycle and cell division (FIG. 5B).

Figure 5C:
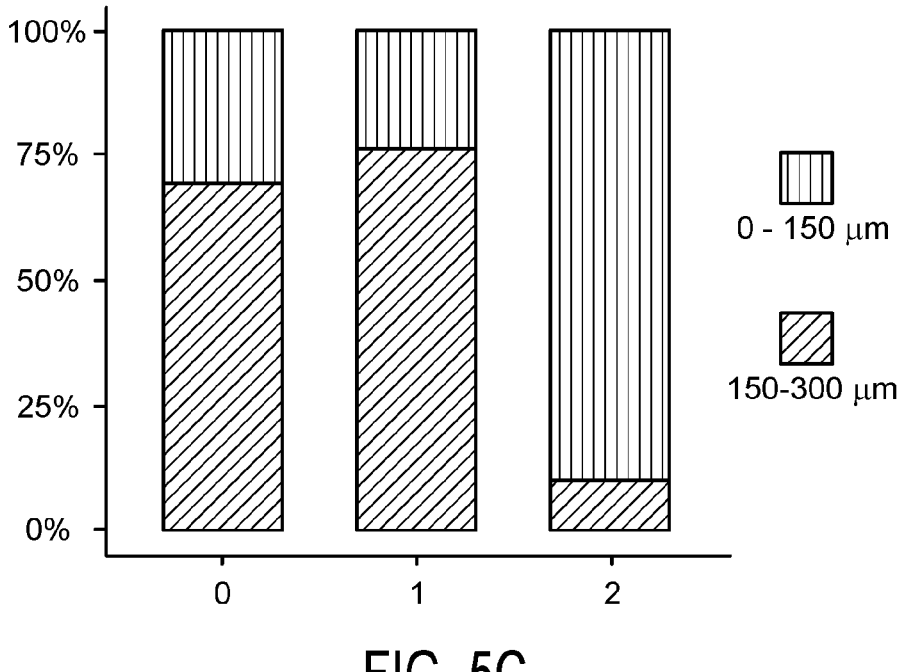
FIG. 5C depicts gene clustering analysis for cells from the two tagged regions demonstrating enrichment of cells from region 1 in cluster 2 and inversely for region 2 cells in cluster 1.

Additional dimensional reduction and clustering on was performed on these cells. Three clusters of cells with highly varying regional compositions were observed (FIG. 5C). Notably, cluster 1 and 0 demonstrated a strong majority located in region 2 (distal to edge) and cluster 2 cells were found largely in region 1 (proximal to edge). When differential gene expression analysis was performed, it was found that cluster 1 strongly expressed cell cycle related genes while cluster 2 expressed cytoskeletal and ECM remodeling genes. This suggests that rather than a gradual continuum of expression states, that the cells at the wound edge represent distinct transcriptional programs with a motile, ECM secreting population enriched at the edge while a proliferative population is located behind these cells. These results were confirmed using immunofluorescent staining for Acta2 and Stmn1 which revealed enrichment for Acta2 high expressing cells at the wound edge while the opposite was observed for Stmn1. These results match the observations in FIG. 5A.

Example 3. Demonstration in Lymph Nodes as a Model Tissue

In order to demonstrate the capabilities of the zipcode tag methods in a tissue setting, lymph nodes were selected, given the well-studied organization of immune cell populations in this tissue. Inguinal lymph nodes were extracted from 4-6 week old B6 mice and embedded while live in 2% low melt agarose. 170 um slices were taken using a vibratome. Sections were blocked with PBS+0.1% BSA+1:100 ssDNA for 30 minutes, then stained with antibody-DNA conjugate anchor construct comprising a protected overhang sequence, and tissue was fluorescently labeled anti-CD3e and anti-B220 antibodies for 1.5 hrs at RT. Sections were washed twice in PBS+0.1% BSA for 5 minutes twice. Tissue/agarose discs were then affixed to a LabtTek chamber well and covered with PBS+0.1% BSA. The sections were then imaged and cell zones based on this imaging were delineated: a B cell region (region 1) and a T cell region (region 2). The first region was illuminated with 360 nm light for 1 s, then a first coding segment construct comprising an overhang complementary to that of the foundation construct, added in solution at 1 uM and incubated for 10 minutes at room temperature. After hybridization, this strand was washed out and a blocking strand complementary to the overhang region of the coding construct was added at 0.25 uM, and incubated for a further 10 minutes at room temperature. After a wash step, the process was repeated for region 2 using a second coding construct. Tissue was then dissociated and single, labeledlive cells were sorted using flow cytometry. These cells were the loaded into the 10X pipeline for scRNA-Seq.

Following standard library prep, both the zipcode and cDNA libraries were sequenced and zipcode counts assigned to cells through the shared 10X barcode. Two labelled populations were clearly identified as well as one ambiguous, low read count population. Excluding the small ambiguous population, the labelled population was gated into zipcode 1 or zipcode 2 dominant.

Figure 6A:
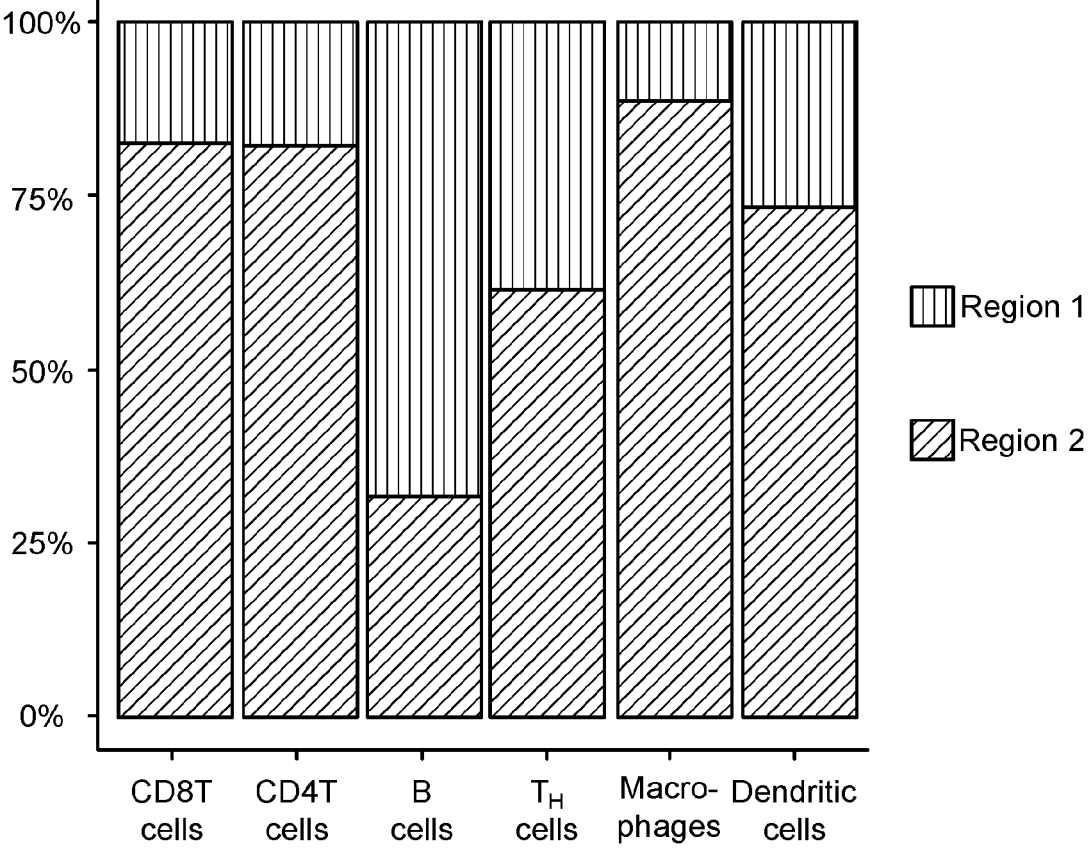
FIG. 6A depicts regional compositions of major populations of immune cells found in the lymph node section.

Transcriptomic data revealed the major and minor immune cell populations expected in the lymph node. Merging these regional identities onto transcriptomic data, it was demonstrated that T cells largely mapped to region 2 or T cell zones and B cells largely mapped to region 1 or B cell zones (FIG. 6A). Other significant cell populations having unique regional identities such as macrophages were strongly localized to region 2.

Figures 6B, 6C:
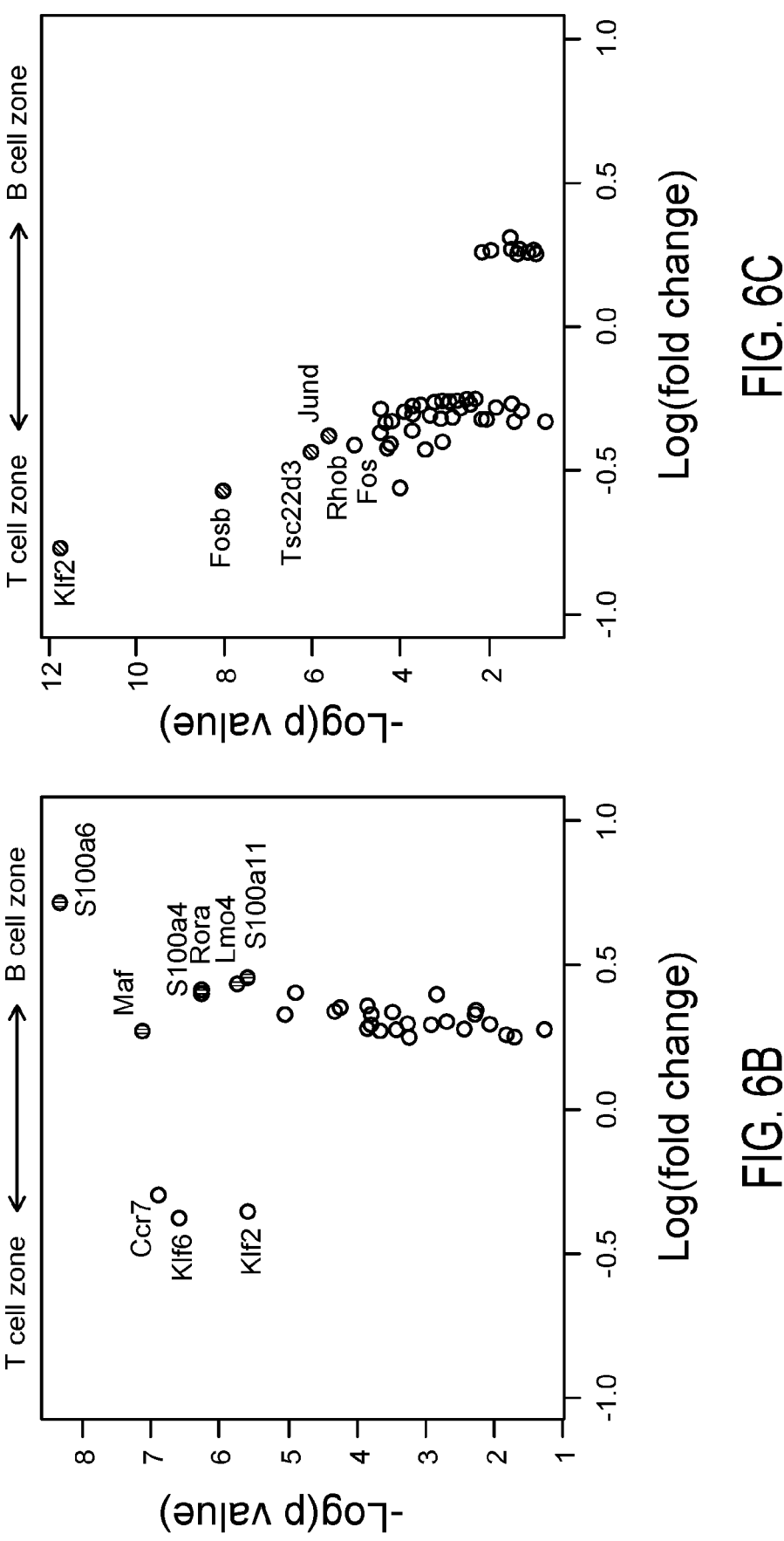
FIG. 6B and depicts gene expression analysis of the CD4 population showing differentially expressed genes between region 1 and region 2 localized cells.

Examining the heterogeneity in cellular localization within the broad populations using differential gene expression, a number of genes were observed to be differentially expressed based on position. Examining only the B cell population, genes such as Klf2, Jund, Fosb were expressed more highly in B cells found in region 2. Validating this observation, imaging of a Klf2-GFP reporter mouse lymph node demonstrated enhanced expression of GFP-Klf2 in B cells found in the T cell zone compared to those found deeper in B cell follicles. Similarly, analysis of the CD4 population yielded a list of differentially expressed genes between region 1 and region 2 localized cells (FIG. 6B). Again, it was observed that Klf2 was more highly expressed on CD4+ T cells from region 2 vs. 1. This was validated again using imaging of KLF2-GFP reporter mouse lymph node sections. Meanwhile CD4 T cells from region 1 preferentially expressed genes such as S100a4, S100a6, and S100a11 and Rora. S100a4/6/11 are of particular interest given recent work tying their expression to a signature for T follicular regulatory cells which would match with the observations herein. In conclusion, this experiments demonstrate that the zipcode tag approach is capable of defining regions correlated with microscopy data and has the ability to identify differential localization of cell populations and differential gene expression based on position within these populations.

Example 4. Branched Coding Segments

In order to achieve combinatorial labeling of regions without the need for strand ligation or the use of many unique photocaged overhang sequences, a strategy was designed that uses a single photocaged strand hybridized to an array of readout 'zipcode' strands; each duplex forms a zipcode 'block' (FIGS. 7A, 7B, and 7C).

Figures 8A, 8B, 8C, 8D:
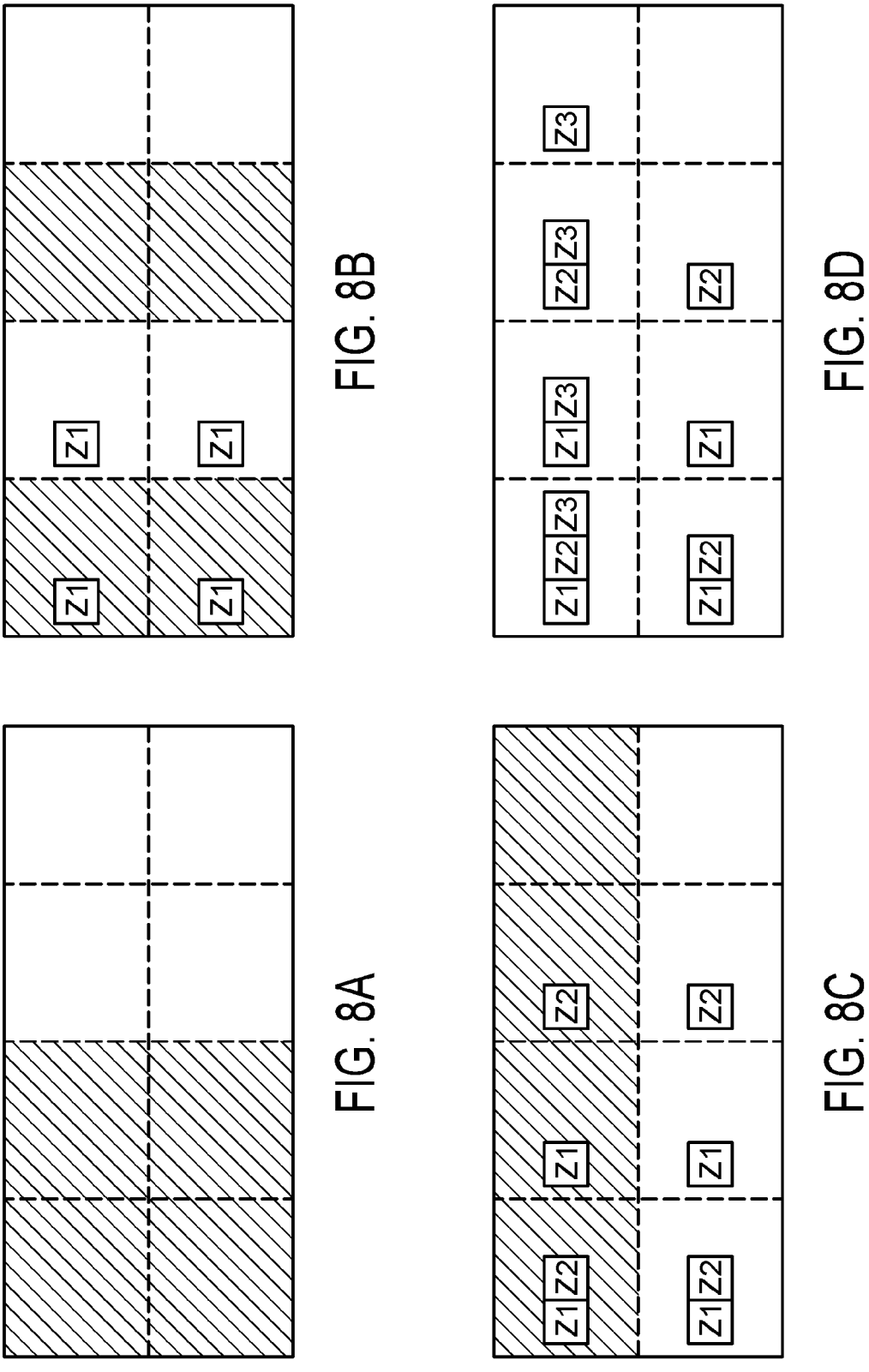
FIG. 8A-8D depict an illumination and synthesis scheme for the addition of coding segments for 8 sectors. Circles depict photolabile protection groups.
Figure 10:
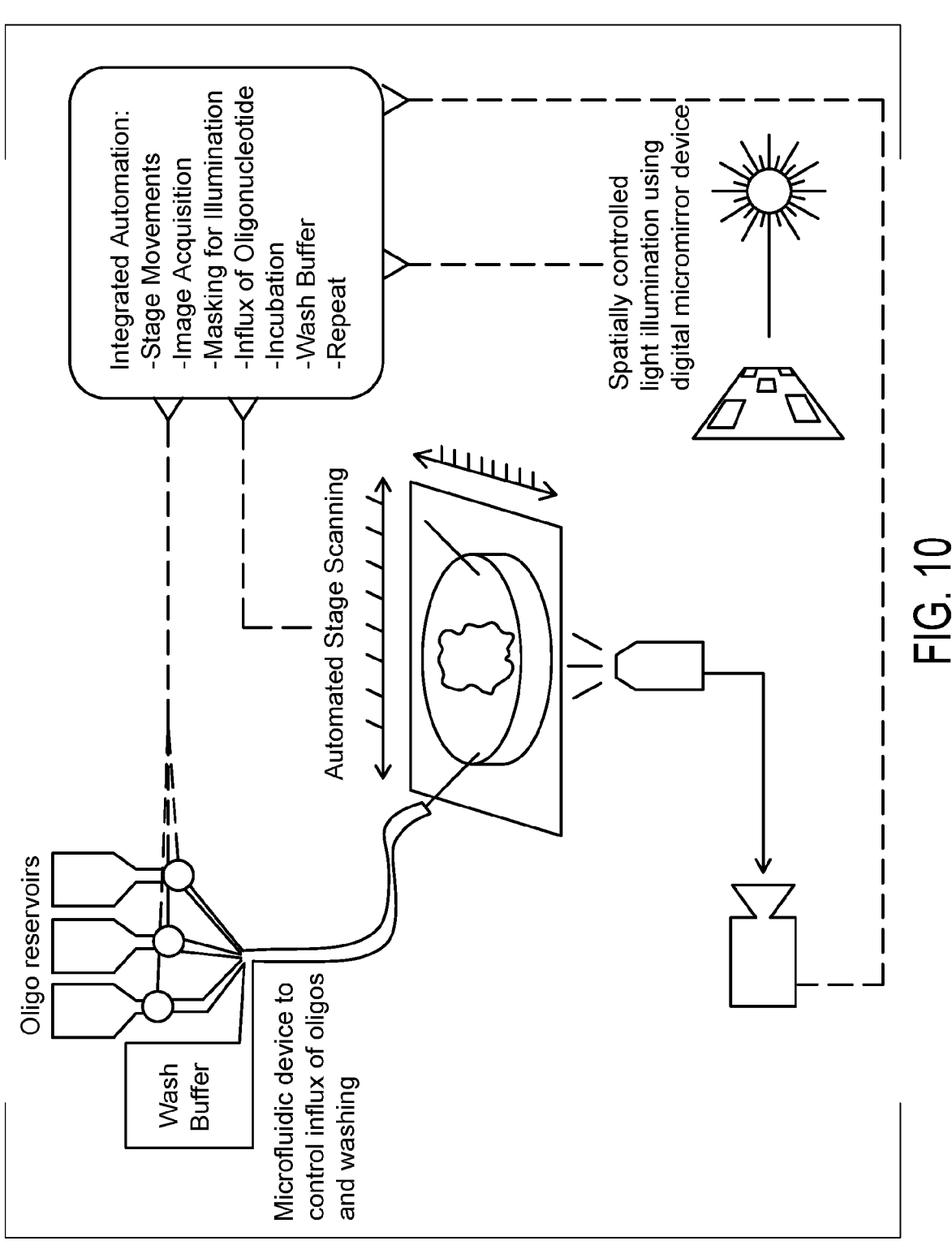
FIG. 10 is a diagrammatic depiction of a zipcode tag synthesis system.

UV illumination controls the addition of new zipcode blocks (FIG. 7D), thus a region can be defined by the presence or absence of a particular zipcode. For example, FIG. 8A-8D depict a synthesis scheme for the addition of coding segments ZC1, ZC2, and ZC3, wherein a tissue section or field of cells is defined into eight sectors comprising two rows of four sectors. As in FIG. 8A, following binding of an anchor construct to the cells in the eight sectors, the two left hand columns are illuminated (shading), followed by application of coding block ZC1, resulting in hybridization of block ZC1 to the anchor construct in the two left hand columns (FIG. 8B). Illumination of the first and third columns (FIG. 8B, shading), followed by application of coding block ZC2 results in its addition to the illuminated sectors (FIG. 8C). Illumination of the top row (FIG. 8C, shading), followed by application of coding segment ZC3, results in its incorporation in the illuminated sectors. The resulting tissue comprises eight sectors having different combinations of zipcode tags (FIG. 8D), using three coding blocks and three illumination steps. The 8 region segmentation was demonstrated using three distinct fluorophores attached to ZC1-3 blocks. Good definition of 8 regions was observed in a dish of cells with cells in each region bearing a unique fluorophore/color combination.

During reverse transcription (FIG. 7E), these zipcode blocks are read out, creating a library of zipcode reads tied to a cell's cDNA. By performing log—normalization on read counts for each zipcode, the unique zipcode sequence can be determined and thus the region that the cell originated from.

In order to demonstrate that these zipcodes can be read out by 10X sequencing, zipcode labeling was performed in-tube for several populations of immune cells, as specified in FIG. 9. These populations received combinatorial sequence of illumination during each round of zipcode addition. Following sequencing, four populations could be identified based on the presence or absence of zipcode 1 or 2. When the combinatorial zipcode identity was compared to transcriptional data, a strong correlation was found with minimal error rate.

Thus it was demonstrated that the approach disclosed herein can spatially define an exponentially increasing number of regions using the branched coding block design, but also that these zipcodes are compatible with 10X scRNA-Seq and can be used to determine a cell's unique zipcode combination. This methodology can be scaled up using more zipcode sequences and rounds of illumination, enabling mapping of single cell transcriptomes with high spatial resolution on the cell-scale level (tens of microns). For example, using 12 zipcode sequences, $2^{12}$ (4,096) 50×50 um regions can be uniquely tagged, resulting a total area of 10.24 mm$^2$.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

The invention claimed is:

1. A method of measuring one or more parameters of interest in individual cells of a sample comprising a multicellular structure and of mapping the one or more measured parameters to the position of the individual cells in the sample, comprising the steps of obtaining a sample comprising a multicellular structure;

identifying multiple sectors of cells based on physical positions of the cells within the sample;

labeling individual cells in each sector of the multiple sectors with an identifier, wherein the identifier for each sector includes one or more unique coding segments, wherein the cells of at least one of the multiple sectors is labeled with an identifier having at least two coding segments with different coding sequences;

dissociating the cells of the sample into individual cells and performing a single cell analysis wherein, for each individual cell, the identifier applied to the individual cell is determined and the one or more parameters is measured; and by the association between the multiple sectors of the sample and the identifiers present on the individual cells, generating a map of the one or more measured parameters across the sample wherein a position of the individual cells prior to the dissociation are determined based on an association between an ordering of the one or more unique coding segments and a position in the sample.

2. The method of claim 1, wherein the sample comprises a tissue section, tumor cells, or cultured cells.

3. The method of claim 1, wherein the one or more measured parameters comprises a transcriptome analysis.

4. The method of claim 1, wherein the one or more measured parameter is selected from the group consisting of a genomic analysis, proteomic analysis, lipidomic analysis, or metabolomic analysis.

5. The method of claim 1, wherein the labeling of individual cells in each sector is achieved by the use of an anchoring moiety comprising a lipid or an antibody that binds to cell surface epitopes.

6. The method of claim 1, wherein the identifiers comprise oligonucleotide constructs, the one or more measured parameters comprises a transcriptome analysis, and the determination of the identifiers applied to the individual cells is achieved by the sequencing process of the transcriptome analysis.

7. The method of claim 6, wherein the cells are labeled with identifiers by a process comprising the steps of:

exposing the sample to a solution comprising a foundation construct comprising an anchoring moiety and an oligonucleotide sequence comprising an overhang, wherein the overhang is functionalized with photolabile protection groups that inhibit hybridization of the overhang with complementary oligonucleotide sequences;

allowing the sample and foundation construct to incubate for a period of time sufficient for the anchoring moieties of the foundation constructs to bind to cells in the sample;

illuminating one or more selected sites in the sample with an energy source that cleaves photolabile protection groups from the applied oligonucleotide sequences present in the one or more sites;

exposing the sample to a solution comprising a coding segment, the coding segment comprising an unprotected overhang comprising a sequence which is complementary to the overhang sequence of the foundation construct, a double stranded coding sequence, a polyadenine strand or sequencing platform capture sequence, and one or more fluorophores;

applying a wash step to remove unbound coding segments; and repeating one or more times the cycle of the previous three steps wherein coding segments comprising a plurality of unique coding sequences are applied in the one or more cycles.

8. The method of claim 6, wherein one or more intervening adapter elements comprising orthogonal overhang sequences are utilized in the synthesis of the oligonucleotide identifiers.

9. The method of claim 6, wherein the cells are labeled with identifiers by a process comprising the steps of exposing the sample to a solution comprising a foundation construct comprising an anchoring moiety and an oligonucleotide sequence comprising an overhang comprising a first overhang sequence, wherein the overhang is functionalized with photolabile protection groups that inhibit hybridization of the overhang with complementary oligonucleotide sequences;

allowing the sample and foundation construct to incubate for a period of time sufficient for the anchoring moieties of the foundation constructs to bind to cells in the sample;

illuminating one or more selected sites in the sample with an energy source that cleaves photolabile protection groups present in the one or more sites;

exposing the sample to a solution comprising a coding segment, the coding segment comprising an oligonucleotide comprising a first and a second strand, wherein the first strand comprises an unprotected overhang comprising a second overhang sequence which is complementary to the first overhang sequence, a short spacer sequence that is hybridized to a complementary spacer sequence on the second strand, a coding sequence, a polyadenine tail or sequencing platform capture sequence, and one or more fluorophores, and wherein the second strand comprises a spacer sequence hybridized to the complementary spacer sequence of the first strand, and an overhang comprising the first overhang sequence, wherein the overhang is functionalized with photolabile protection groups that inhibit hybridization of the overhang with complementary oligonucleotide sequences;

applying a wash step to remove unhybridized coding segments; and repeating one or more times the cycle of the previous three steps; wherein coding segments comprising a plurality of unique coding sequences are applied over the one or more cycles.

10. The method of claim 9, wherein one or more intervening adapter elements comprising orthogonal overhang sequences are utilized in the synthesis of the oligonucleotide identifiers.

11. The method of claim 1, wherein each of the coding segments is branched coding segment including first and second strands of oligonucleotides.

12. The method of claim 1, wherein each of the coding segments includes a fluorophore.

13. The method of claim 1, wherein the cells of a first sector of the multiple sectors are labeled with a first identifier having a first coding segment, wherein the cells of a second sector of the multiple sectors are labeled with a second identifier having the first coding segment and a second coding segment, the first and second coding segments having different coding sequences.

14. The method of claim 13, wherein the cells of a third sector of the multiple sectors are labeled with a third identifier having the first coding segment, the second coding segment, and a third coding segment, the third coding segment having a different coding sequence than each of the first and second coding segments.

15. The method of claim 13, further comprising labeling one or more additional sectors of the multiple sectors with corresponding identifiers having corresponding additional one or more additional coding segments having corresponding different coding sequences than each of the first, second and third coding segments.

* * * * *